United States Patent
Parker (10) Patent No.: US 8,532,322 B2
(45) Date of Patent: Sep. 10, 2013

(54) BONE CONDUCTION DEVICE FOR A SINGLE SIDED DEAF RECIPIENT

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 154 days.

(21) Appl. No.: 12/935,895

(22) PCT Filed: Mar. 31, 2009

(86) PCT No.: PCT/US2009/038884
§ 371 (c)(1), (2), (4) Date: Sep. 30, 2010

(87) PCT Pub. No.: WO2009/124008
PCT Pub. Date: Oct. 8, 2009

(65) Prior Publication Data
US 2011/0026748 A1 Feb. 3, 2011

Related U.S. Application Data

(60) Provisional application No. 61/041,185, filed on Mar. 31, 2008.

(51) Int. Cl.
*H04R 25/00* (2006.01)

(52) U.S. Cl.
USPC .................... 381/326; 381/312; 381/151

(58) Field of Classification Search
USPC .............. 381/312, 315–317, 320–321, 151, 381/380–381; 600/25; 607/55–57
See application file for complete search history.

(56) References Cited

U.S. PATENT DOCUMENTS

| 3,809,829 A | 5/1974 | Vignini et al. |
| 5,323,468 A | 6/1994 | Bottesch |
| 5,434,926 A * | 7/1995 | Watanabe et al. ............... 381/86 |
| 5,800,475 A | 9/1998 | Jules |
| 5,805,571 A | 9/1998 | Zwan et al. |
| 5,913,815 A | 6/1999 | Ball et al. |

(Continued)

FOREIGN PATENT DOCUMENTS

| WO | WO 91/12783 | 9/1991 |
| WO | WO 99/07311 | 2/1999 |

(Continued)

OTHER PUBLICATIONS

Henry, et al., "Bone Conduction: Anatomy, Physiology, and Communication.", Army Research Laboratory, Aberdeen Proving Ground, MD 21005-5425. May 2007.

(Continued)

*Primary Examiner* — Suhan Ni
(74) *Attorney, Agent, or Firm* — Kilpatrick Townsend & Stockton LLP (57) ABSTRACT

Methods and systems are provided for determining whether signals to be applied by a bone conduction device would be masked by signals arriving at the good ear of a single sided deaf patient. The bone conduction device then applies stimulation for frequency components of the sound received by the bone conduction device that would not be masked by sound received by the patient's good ear. In applying the stimulation, the bone conduction device may apply a gain to compensate for the head shadow effect. This gain may be determined by inverting at least a portion of a curve for the head shadow effect.

20 Claims, 9 Drawing Sheets

(56) References Cited

U.S. PATENT DOCUMENTS

| | | | |
|---|---|---|---|
| 5,991,419 A * | 11/1999 | Brander | 381/312 |
| 6,549,633 B1 * | 4/2003 | Westermann | 381/312 |
| 6,602,202 B2 | 8/2003 | John et al. | |
| 6,643,378 B2 | 11/2003 | Schumaier | |
| 6,840,908 B2 | 1/2005 | Edwards et al. | |
| 7,018,342 B2 | 3/2006 | Harrison et al. | |
| 7,630,507 B2 * | 12/2009 | Kates | 381/312 |
| 2004/0078057 A1 | 4/2004 | Gibson | |
| 2004/0082980 A1 | 4/2004 | Mouine et al. | |
| 2004/0204921 A1 | 10/2004 | Bye et al. | |
| 2005/0171579 A1 | 8/2005 | Tasche et al. | |
| 2006/0018488 A1 | 1/2006 | Viala et al. | |
| 2006/0287689 A1 | 12/2006 | Debruyne et al. | |
| 2008/0212810 A1 * | 9/2008 | Pedersen | 381/312 |
| 2010/0041940 A1 | 2/2010 | Hillbratt et al. | |
| 2011/0022119 A1 | 1/2011 | Parker | |
| 2011/0026721 A1 | 2/2011 | Parker | |
| 2011/0026748 A1 | 2/2011 | Parker | |

FOREIGN PATENT DOCUMENTS

| | | |
|---|---|---|
| WO | WO 2005/029915 | 3/2005 |
| WO | WO 2005/122887 | 12/2005 |
| WO | WO 2007/140367 | 12/2007 |
| WO | WO 2009/124005 | 10/2009 |
| WO | WO 2009/124008 | 10/2009 |
| WO | WO 2009/124010 | 10/2009 |
| WO | WO 2010/017579 | 2/2010 |

OTHER PUBLICATIONS

International Search Report, for PCT/US2009/038884, mailed Jun. 22, 2009.

Henry et al., "Bone Conduction: Anatomy, physiology, and Communication." Army Research Laboratory, Aberdeen Proving Ground, MD 21005-5425. May 2007 (206 pages).

F.M. Vaneecloo et al., "Réhabilitation prothétique B.A.H.A des cophoses unilatérales", Annales D'oto-Laryngies et de Chirurgie Cervicofaciale, vol. 117, No. 6, Dec. 2000, pp. 410-417, 8 pages.

Michael Nolan et al., "Transcranial attenuation in bone conduction audiometry", The Journal of Laryngology and Otology, Jun. 1981, vol. 95, pp. 597-608, 12 pages.

European Patent Application No. 02 736 403.3, Office Communication mailed on Oct. 17, 2008. 6 Pages.

European Patent Application No. 02 736 403.3, Office Communication mailed on Apr. 27, 2009. 4 Pages.

European Patent Application No. 02 736 403.3, Office Communication mailed on Apr. 13, 2010. 6 Pages.

International Application No. PCT/SE02/01089, International Search Report mailed on Oct. 1, 2002. 3 Pages.

International Application No. PCT/SE02/01089, International Preliminary Examination Report mailed on Oct. 6, 2003. 5 Pages.

International Search Report issued by the International Searching Authority in connection with International Patent Application No. PCT/AU2009/001010, mailed Nov. 25, 2009 (4 pages).

International Search Report issued by the International Searching Authority in connection with International Patent Application No. PCT/US2009/038879, mailed May 22, 2009 (1 page).

Written Opinion issued by the International Searching Authority in connection with International Patent Application No. PCT/US2009/038879, mailed May 22, 2009 (4 pages).

Written Opinion issued by the International Searching Authority in connection with International Patent Application No. PCT/US2009/038884, mailed Jun. 22, 2009 (5 pages).

International Search Report issued by the International Searching Authority in connection with International Patent Application No. PCT/US2009/038890, mailed May 29, 2009 (1 page).

Written Opinion issued by the International Searching Authority in connection with International Patent Application No. PCT/US2009/038890, mailed May 29, 2009 (6 pages).

International Preliminary Report on Patentability issued by International Preliminary Examining Authority in connection with International Patent Application No. PCT/US2009/038890, mailed Apr. 15, 2010 (8 pages).

Bernd Edler et al., "ASAC—Analysis/Synthesis Audio Codec for Very Low Bit Rates", 100th AES Convention, Copenhagen (May 1996) (15 pages).

Frank Baumgarte et al., "A Nonlinear Psychoacoustic Model Applied to the ISO MPEG Layer 3 Coder", 99th AES Convention, New York, Oct. 1995 (15 pages).

* cited by examiner

BONE CONDUCTION DEVICE FOR A SINGLE SIDED DEAF RECIPIENT

CROSS-REFERENCE TO RELATED APPLICATIONS

The present application is a National Stage Application of International Application No. PCT/US2009/38884, filed Mar. 31, 2009, and claims the benefit of U.S. Provisional Patent Application 61/041,185; filed Mar. 31, 2008. The contents of these applications is hereby incorporated by reference herein.

BACKGROUND

1. Field of the Invention

The present invention is generally directed to a bone conduction device, and more particularly, to optimization of a bone conduction device for a single sided deaf recipient.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to provide an electrical stimulus directly to the cochlea nerve, thereby causing a hearing sensation.

Conductive hearing loss occurs when the normal mechanical pathways to provide sound to hair cells in the cochlea are impeded, for example, by damage to the ossicular chain or ear canal. Individuals who suffer from conductive hearing loss may still have some form of residual hearing because the hair cells in the cochlea are generally undamaged.

Individuals who suffer from conductive hearing loss are typically not considered to be candidates for a cochlear implant due to the irreversible nature of the cochlear implant. Specifically, insertion of the electrode array into a recipient's cochlea results in the destruction of a majority of hair cells within the cochlea. This results in the loss of residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Furthermore, hearing aids are typically unsuitable for individuals who suffer from single sided deafness (total hearing loss only in one ear) or individuals who suffer from mixed hearing losses (i.e., combinations of sensorineural and conductive hearing loss).

When an individual having fully functioning hearing receives an input sound, the sound is transmitted to the cochlea via two primary mechanisms: air conduction and bone conduction. As noted above, hearing aids rely primarily on the principles of air conduction. In contrast, other devices, referred to as bone conduction devices, rely predominantly on vibration of the bones of the recipients skull to provide acoustic signals to the cochlea.

Those individuals who cannot derive suitable benefit from hearing aids may benefit from bone conduction devices. Bone conduction devices convert a received sound into a mechanical vibration representative of the received sound. This vibration is then transferred to the bone structure of the skull, causing vibration of the recipient's skull. This skull vibration results in motion of the fluid of the cochlea. Hair cells inside the cochlea are responsive to this motion of the cochlea fluid, thereby generating nerve impulses, which result in the perception of the received sound.

Particular hearing impaired individuals who may benefit from a bone conduction device are those individuals who suffer from single sided deafness. Single sided deafness, also known as monaural hearing, or unilateral hearing loss (UHL), is the total or substantial lose of conductive and sensorineural hearing in one ear. Typically, the individual has normal or undamaged hearing in the second ear. Causes of single sided deafness may include, for example, measles, mumps, trauma, tumors, hereditary disorders, etc.

SUMMARY

In one aspect of the invention, a method for operating a bone conduction device fitted to a deaf ear of a patient having a second function ear is provided. The method comprises: receiving a sound at the deaf ear, wherein the sound has a plurality of frequency components; generating an estimate of sound received at a second ear of the patient; determining, based on the estimate, whether the sound received at the second ear would mask one or more of the frequency components of the sound received at the deaf ear; and determining a set of bone conduction stimulation signals based only on frequency components of the sound received at the deaf ear that would not be masked by the sound received at the second ear.

In a second aspect, a bone conduction device configured to be fitted to a deaf ear of a patient having a second function ear is provided. The device comprises: a sound input device configured to receive, at the deaf ear, a sound having a plurality of frequency components; an electronics module configured to generate an estimate of sound received at a second ear of the patient, and configured to determine, based on the estimate, whether the sound received at the second ear would mask one or more of the frequency components of the sound received at the first ear, and configured to determine a set of bone conduction stimulation signals based only on one or more frequency components of the sound received at the deaf ear that would not be masked by the sound received at the second ear.

In a third aspect, there is provided a bone conduction device configured to be fitted to a deaf ear of a patient having a second functional ear. The device comprises: means for receiving a sound having a plurality of frequency components; means for generating an estimate of sound received at a second ear of the patient; means for determining, based on the estimate, whether the sound received at the second ear would mask one or more of the frequency components of the sound received at the deaf ear; and means for determining a set of bone conduction stimulation signals based only on frequency components of the sound received at the deaf ear that would not be masked by the sound received at the second ear.

BRIEF DESCRIPTION OF THE DRAWINGS

Embodiments of the present invention are described herein in conjunction with the accompanying drawings, in which.

DETAILED DESCRIPTION

In an embodiment, a bone conduction device is fitted to a deaf ear of a singled sided deaf patient having a second functional ear. The bone conduction device may determine whether signals to be applied by a bone conduction device would be masked by signals arriving at the good ear of the single sided deaf patient. The bone conduction device then applies stimulation for frequency components of the sound received by the bone conduction device that would not be masked. In applying the stimulation, the bone conduction device may apply a gain to compensate for the head shadow effect.

Figure 1:
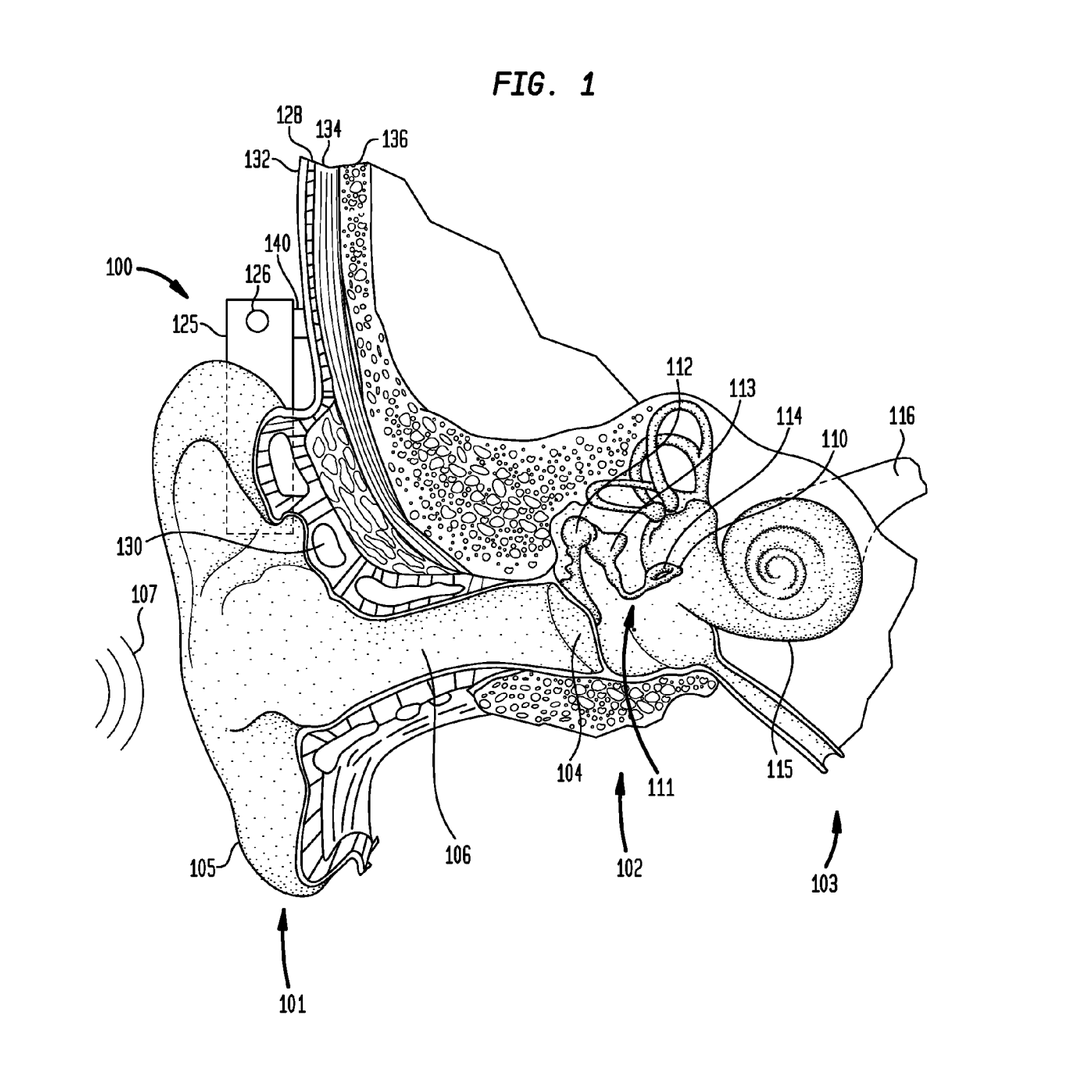
FIG. 1 is a perspective view of an exemplary medical device, namely a bone conduction device, in which embodiments of the present invention may be advantageously implemented.

FIG. 1 is a cross sectional view of a human ear and surrounding area, along with a side view of an embodiment of a bone conduction device 100. Bone conduction device 100 is shown coupled to a recipient having an outer ear 101, a middle ear 105 and an inner ear 107. Components of outer ear 101, middle ear 105 and inner ear 107 are described below, followed by a description of mechanical stimulator 100.

In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. The motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 is a cross sectional view of a human ear and surrounding area, along with a side view of an embodiment of a bone conduction device 100. Bone conduction device 100 is shown coupled to a recipient having an outer ear 101, a middle ear 102 and an inner ear 103. Components of outer ear 101, middle ear 102 and inner ear 103 are described below, followed by a description of mechanical stimulator 100.

In the embodiments illustrated in FIG. 1, bone conduction device 100 comprises a housing 125 having at least one microphone 126 positioned therein or thereon. Housing 125 is coupled to the body of the recipient via coupling 140. As described below, bone conduction device 100 may comprise a signal processor, a transducer, transducer drive components and/or various other electronic circuits/devices.

In accordance with embodiments of the present invention, an anchor system (not shown) may be implanted in the recipient. The anchor system may be fixed to bone 136. In various embodiments, the anchor system may be implanted under skin 132 within muscle 134 and/or fat 128 or the hearing device may be anchored in another suitable manner. In certain embodiments, a coupling 140 attaches device 100 to the anchor system.

Figure 2A:
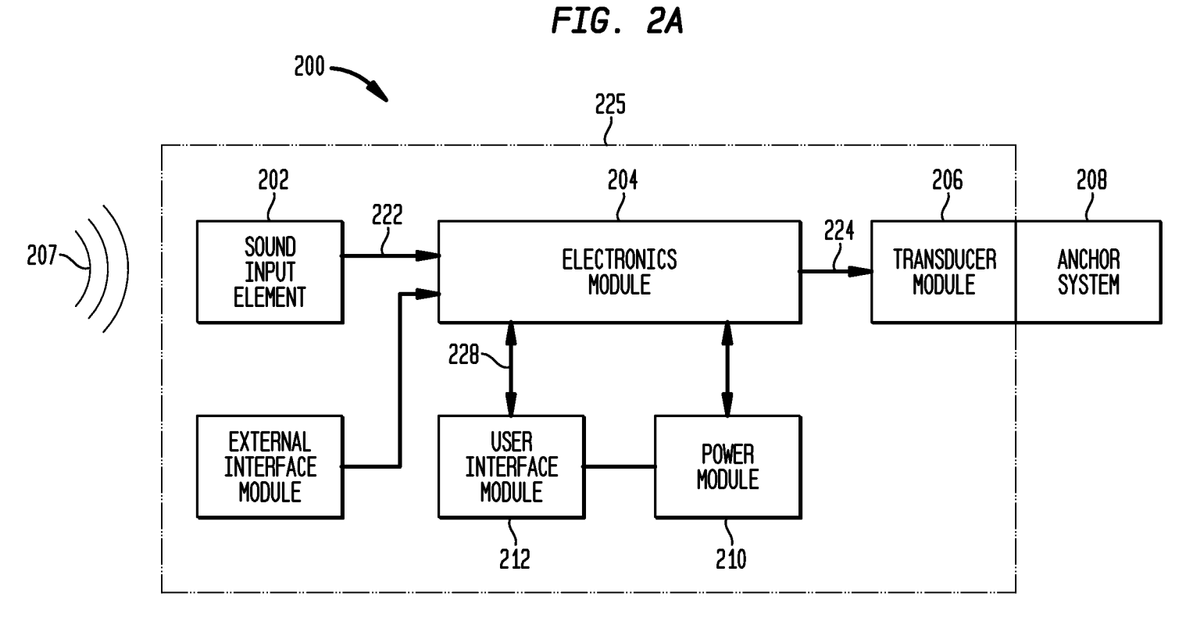
FIG. 2A is a high-level functional block diagram of a bone conduction device, such as the bone conduction device of FIG. 1, in accordance with an embodiment.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipients skull, thereby activating the hair cells in the recipient's cochlea (not shown) via cochlea fluid motion.

FIG. 2A also illustrates a power module 210. Power module 210 provides electrical power to one or more components of bone conduction device 200. For ease of illustration, power module 210 has been shown connected only to user interface module 212 and electronics module 204. However, it should be appreciated that power module 210 may be used to supply power to any electrically powered circuits/components of bone conduction device 200.

Bone conduction device 200 further includes a user interface module 212 that allows the recipient to interact with device 200. For example, user interface module 212 may allow the recipient to adjust the volume, alter the speech processing strategies, power on/off the device, etc. User interface module 212 communicates with electronics module 204 via signal line 228.

Bone conduction device 200 may further include an external interface module 214 that may be used to connect electronics module 204 to an external device, such as a fitting system. Using external interface module 214, the external device, may obtain information from the bone conduction device (e.g., the current parameters, data, alarms, etc.) and/or modify the parameters of the bone conduction device 200 used in processing received sounds.

In the embodiment illustrated in FIG. 2A, sound input element 202, electronics module 204, transducer 206, power module 210, user interface module 212, and external interface module 214 been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
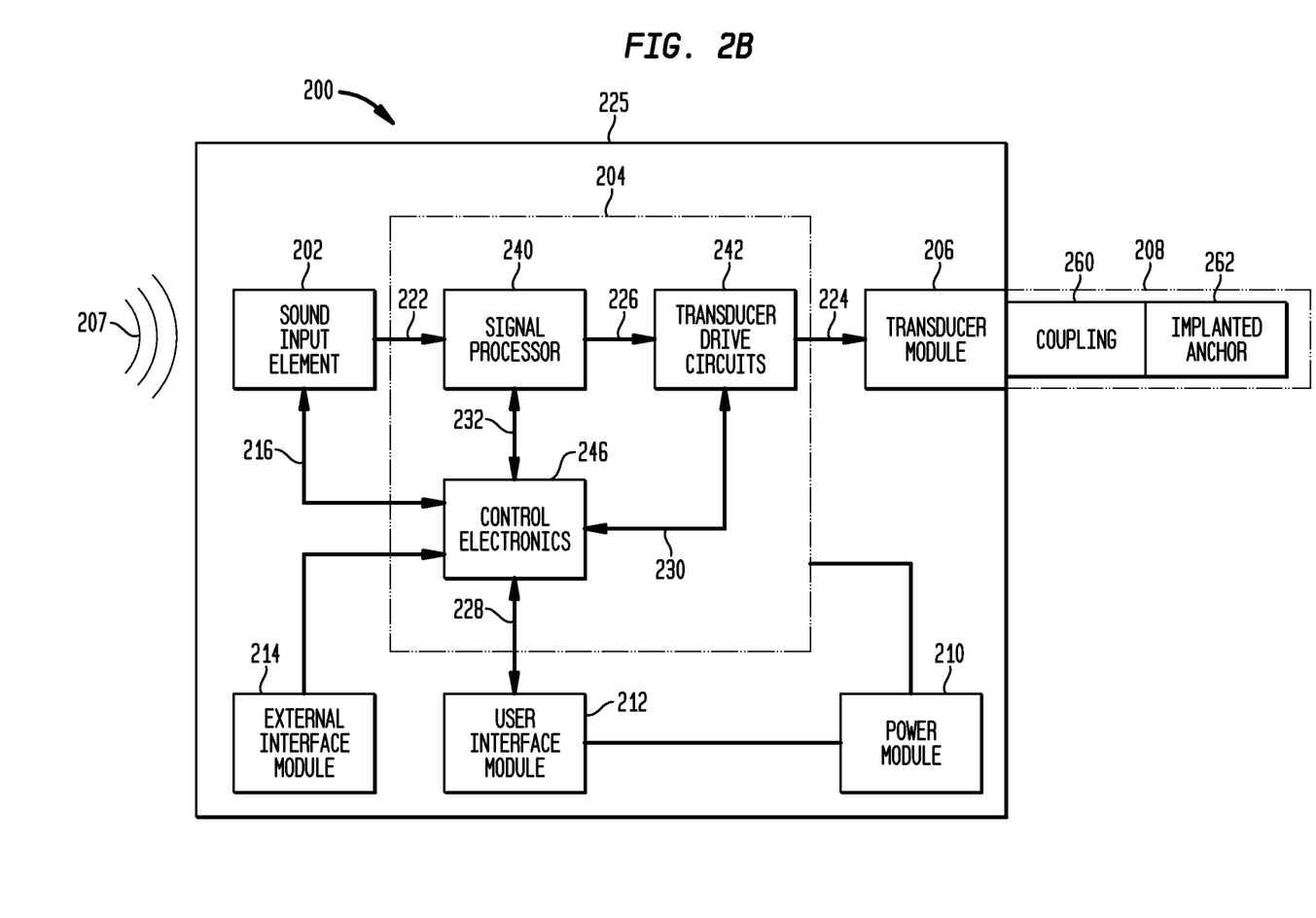
FIG. 2B is detailed functional block diagram of the bone conduction device illustrated in FIG. 2A, in accordance with an embodiment.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient. For ease of description, the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As shown, control electronics 246 may be connected to one or more of user interface module 212, external interface module 214, sound input element 202, sound processor 240 and/or transducer drive components 242. In embodiments, based on inputs received at user interface module 212 or external interface module 214, control electronics 246 may provide instructions to, or request information from, other components of bone conduction device 200.

As noted above, a recipient may control various functions of the device via user interface module 212. User interface module 212 includes one or more components that allow the recipient to provide inputs to, or receive information from, elements of bone conduction device 200. Further, as noted above, external interface module 214 may be used to connect electronics module 204 to an external device, such as a fitting system. Using external interface module 214, a fitting system may be able to obtain and/or modify information for the various components of bone conduction device 200. For example, in an embodiment, a fitting system may use external interface module 214 to obtain and modify the parameters of sound processor 240 used in processing, amplifying, and filtering the received sound. External interface module 214 may comprise a plug for permitting a wired connection between bone conduction device and an external device, or, for example, wireless communications hardware and/or software to permit a wireless connection between bone conduction device and an external device. Such a wireless connection may use any appropriate wireless mechanism, such as, for example, Wi-Fi (IEEE 802.11), Bluetooth, etc.

Figure 3:
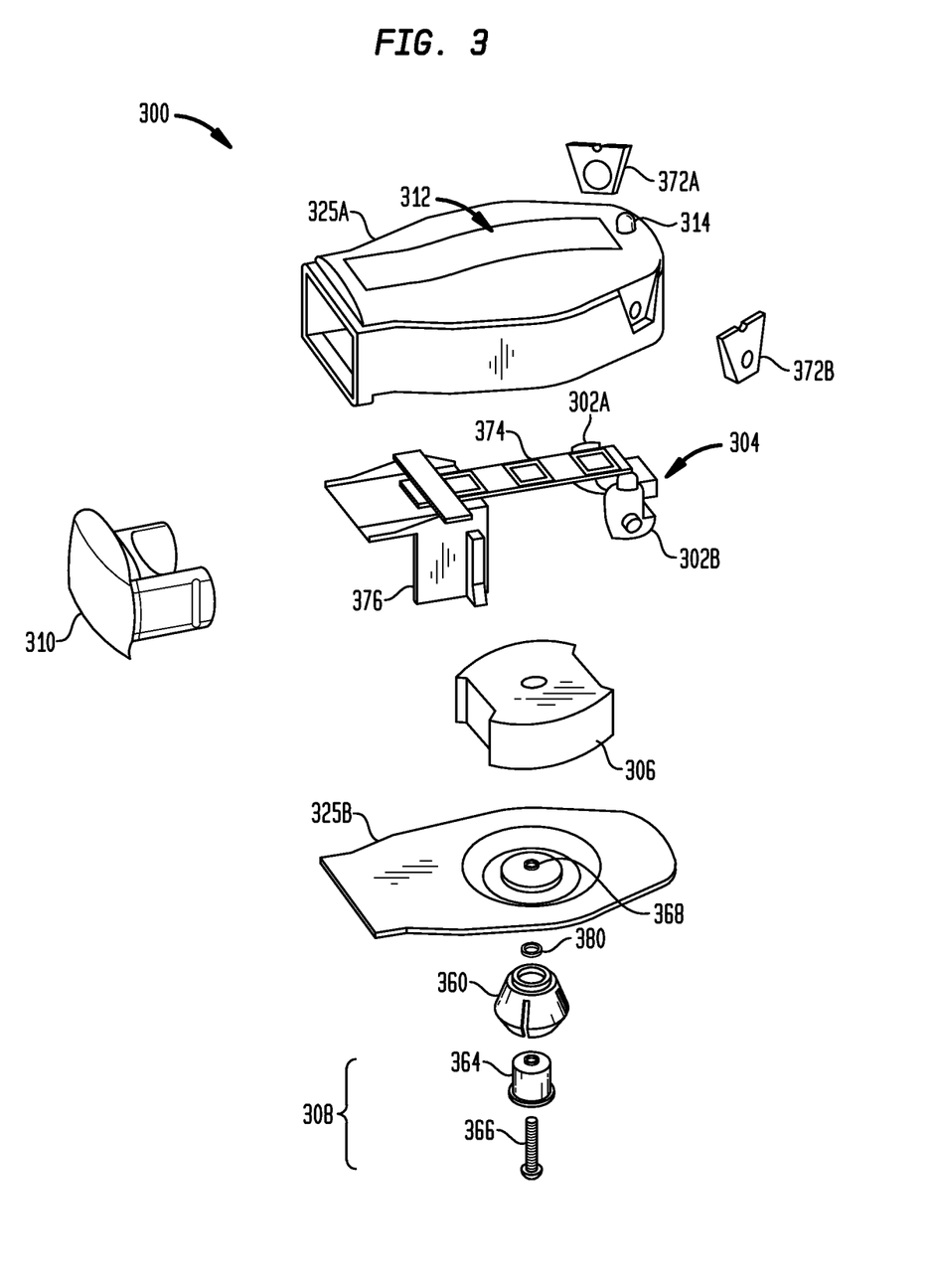
FIG. 3 is an exploded view of an embodiment of a bone conduction device in accordance with one embodiment of FIG. 2B.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, electronics module 304 may include a sound processor, transducer drive components and control electronics. These components may be separate components or included in a single component (e.g., a processor, ASIC, etc.).

In the illustrated embodiment, electronics module 304 includes a printed circuit board 374 (PCB) to electrically connect and mechanically support the components of electronics module 304. Attached to PCB 374 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 374 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of user interface module 212, referred to herein as user interface module 312. User interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

Bone conduction device 300 further includes an embodiment of external interface module 214, referred to herein as external interface module 314. External interface module 314 may include a jack connector for receiving a plug for a wired connection to an external device, such as a fitting system, FM hearing system, MP3 player, television, mobile phone, etc. Or, for example, external interface module 314 may comprise hardware and/or software for wirelessly connecting to an external device. In still other embodiments, a further sound input element in the form of a telecoil (not shown) may be integrated in, or connected to, bone conduction device 300. In such embodiments, the telecoil permits bone conduction device 300 to receive input signals from, for example, a telephone or other similar device.

Sounds originating on one side of a patient's head may be obstructed by the patient's head when traveling through and around a patient's head to the ear located on the opposite side of the patient's head from the sound's source. This is known as the "head shadow" effect, and the obstruction caused by the head may result in a significant attenuation (i.e., reduced amplitude) of the intensity of the sound. Additionally, the obstruction may also result in a filtering effect on the sound that may cause a patient to have perception problems with linear distance and the direction of the sound.

Figure 4A:
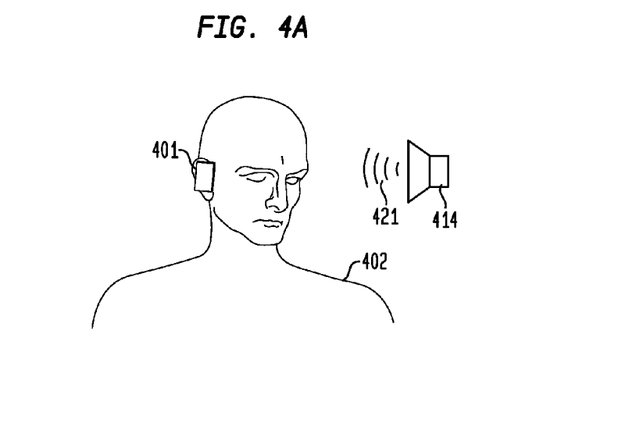
FIG. 4A provides a simple diagram for illustrating the head shadow effect in a patient with single sided deafness (SSD), in accordance with an embodiment.
Figure 4B:
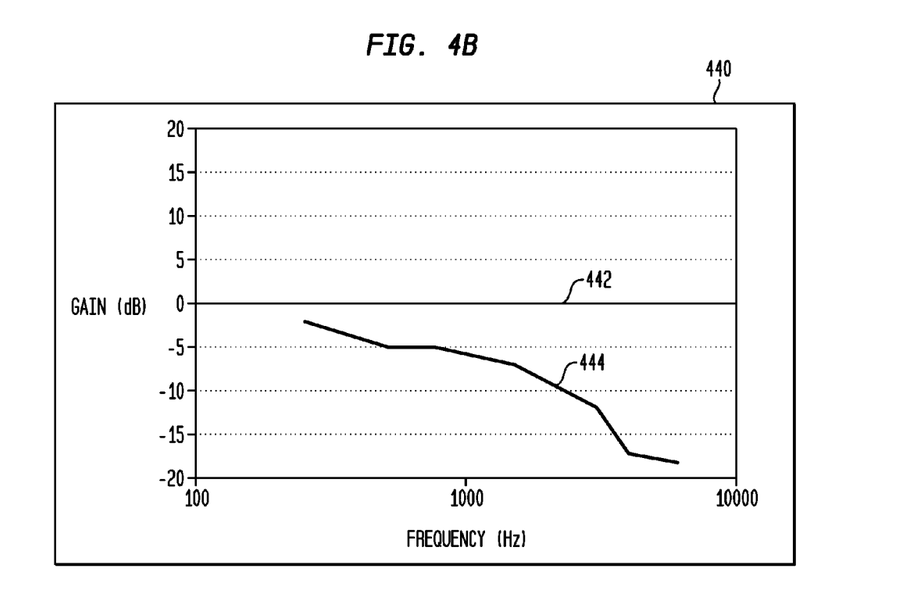
FIG. 4B illustrates an exemplary curve of the attenuation versus frequency of the sound arriving at a bone conduction device in the system of FIG. 4A, in accordance with an embodiment.

FIGS. 4A-4B provide a simple diagram for illustrating the head shadow effect in a patient with single sided deafness (SSD). As shown in FIG. 4A, a sound source 414 may generate a sound 421 on the side of a patient 402, such as the side of the patient's good ear. The patient's head may then obstruct the sound 421 arriving at a bone conduction device 401 located on the opposite side of the patients head.

FIG. 4B illustrates an exemplary curve of the attenuation versus frequency of the sound 421 arriving at the bone conduction device 401. In this example, sound 421 is illustrated by curve 442 and is a constant amplitude sound over frequencies from 100 to 10,000 Hz. Curve 444 illustrates the sound arriving at the bone conduction device 401. As illustrated, the attenuation of the sound 421 caused by the patient's head varies by frequency and higher frequencies are generally attenuated more than lower frequency sounds.

In an embodiment, the bone conduction device 401 may account for the head shadow effect in applying stimulation to the patient. Bone conduction device 401 may use various techniques in compensating for the head shadow effect. In a first example, bone conduction device 401 may apply a constant gain to received sound signals that is equal to the maximum attenuation due to the head shadow effect. For example, in curve 444, the maximum attenuation due to the head shadow effect in this example, is −20 db. As such, in this first example, bone conduction device may apply a gain of 20 dB to received sounds to compensate for the head shadow effect. It should be noted that this is but one example and in other embodiments, bone conduction device 401 may apply a different gain (e.g., 70 dB), or, for example, bone conduction device 401 may apply a gain that is less than the maximum attenuation due to the head shadow effect. Further, in embodiments, the patient may be able to adjust the gain of the bone conduction device 401 using a user interface of the bone conduction device 401.

In a second example, bone conduction device 401 may apply a gain to the sound received at bone conduction device 401 that may mirror the attenuation resulting from the head shadow effect, such as illustrated in exemplary curve 444. For example, due to the head shadow effect, the patient's skull may absorb different frequencies of stimulation applied to patient differently. Thus, a constant gain amplifier (i.e., an amplifier that applies constant gain across all frequencies of sound received by the bone conduction device) may distort sound as perceived by the patient. Referring to the head shadow curve 421, it is apparent that lower frequency sounds are less impacted by the head shadow effect than higher frequency sounds. Thus, if bone conduction device 401 applies a constant gain to all frequencies, the lower frequency sounds may be perceived as louder than higher frequency sounds even if they arrived at the bone conduction device with the same amplitude.

Figure 5A:
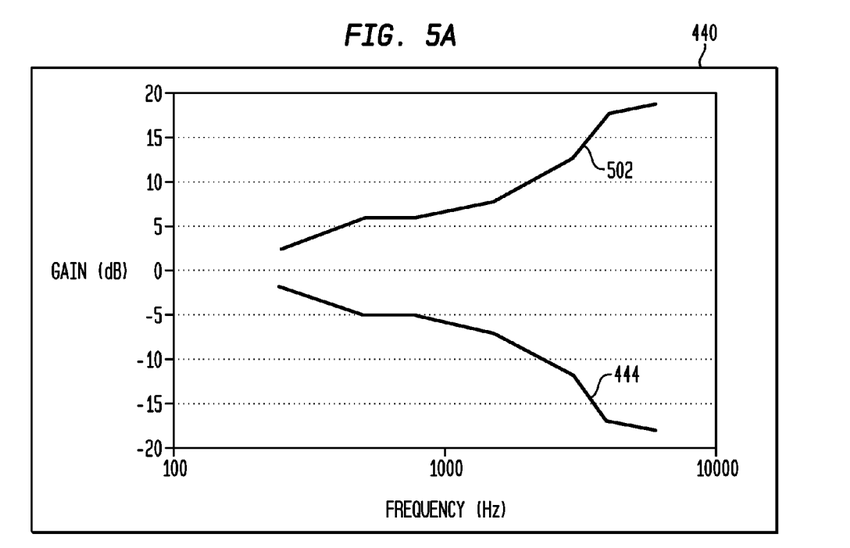
FIG. 5A illustrates an exemplary gain curve that a bone conduction device may apply to compensate for the head shadow effect, in accordance with an embodiment.

FIG. 5A illustrates an exemplary gain curve 502 that a bone conduction device may apply to compensate for the head shadow effect, in accordance with an embodiment. As illustrated, the gain applied by the bone conduction device increases with frequency. Further, this gain curve may be obtained by simply inverting the head shadow curve, which may be a curve generic for all persons, or a population of persons sharing one or more common characteristics (e.g., a curve for children, a curve for elderly males, etc.). Or, for example, in an embodiment, the head shadow curve may be specific for the individual. For example, during a fitting process, the head shadow for the individual may be measured.

Figure 5B:
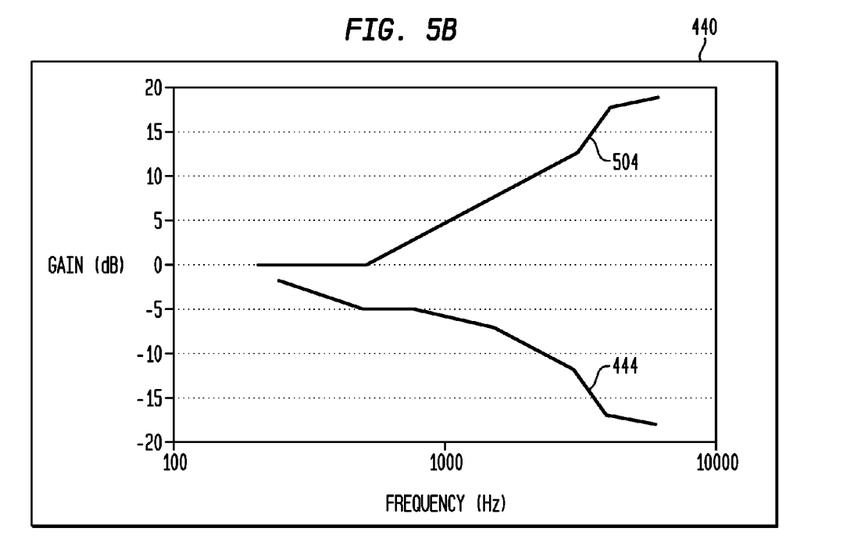
FIG. 5B illustrates an exemplary gain curve that is an inverse of the head shadow effect at higher frequencies, but applies a lower gain at lower frequencies, in accordance with an embodiment.

In a third example, the bone conduction device 401 may apply a gain curve that is an inverse of the head shadow effect at higher frequencies but applies less of a gain or no gain at lower frequencies. FIG. 5B illustrates an exemplary gain curve 504 that is an inverse of the head shadow effect at higher frequencies, but applies a lower gain at lower frequencies.

In applying the gain, such as gain curves 502 or 504, bone conduction device 401 may receive a sound and split the received sound into a number of frequency bins. For example, bone conduction device 401 may convert the received time domain sound signal to the frequency domain using for example a fast Fourier transform (FFT) and then divide the signal into a plurality of frequency bins. Then, bone conduction device 401 may apply a gain to the amplitude for each frequency bin in accordance with the gain of gain curve 502 or 504 for the frequencies corresponding to the frequency bin. Then bone conduction device 401 may convert the signal back to the time domain. After which, bone conduction device 401 may apply stimulation to the patient in accordance with the time domain signal. It should be noted that this is but one technique that bone conduction device 401 may use to apply gain to a received audio signal, and in other embodiments, bone conduction device 401 may use other techniques to apply gain to the received signal to compensate for the head shadow effect.

In an embodiment for a patient suffering from single side deafness, the bone conduction device 401 may only apply stimulation for sounds that are not masked by sounds arriving at the patient's good ear. For example, the bone conduction device 401 may estimate or determine the sound arriving at the good ear and then, use the estimate, to determine if the sound arriving at the good ear would mask sounds, or frequency components, arriving at the patient's bad or deaf ear. Then, bone conduction device 401 may only apply stimulation for unmasked sounds or frequency components. By not applying stimulation for masked sounds, the bone conduction device 401 may conserve power. This power savings for the bone conduction device may enable the bone conduction device 401 to have longer battery life and/or the ability to apply more intense stimulation.

Bone conduction device 401 may use various techniques for determining or estimating the sound arriving at the patient's good ear. In a first example, bone conduction device 401 may use a microphone (not shown) located on the side of the good ear to receive information regarding sounds arriving at the patient's good ear. This microphone may communicate with the bone conduction device 401 via a wired or wireless connection.

Figure 6:
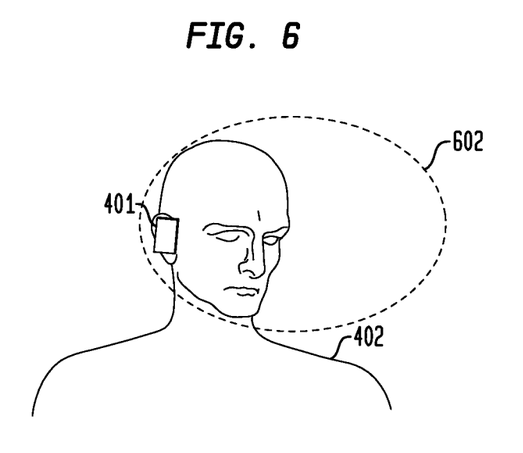
FIG. 6 illustrates an exemplary beam shape that a bone conduction device may use to receive sounds originating on the opposite side of the patient's head, in accordance with an embodiment.

In a second example, bone conduction device 401 may compensate for the head shadow effect by employing two or more microphones configured as a directional microphone with a beam shape directed towards the patient's good ear. FIG. 6 illustrates an exemplary beam shape 601 that a bone conduction device 401 may use to receive sounds originating on the opposite side of the patient's head, in accordance with an embodiment. Bone conduction device 601 may use various techniques for employing a directional microphone with a beam shape directed towards the patient's good or functional ear. For example, bone conduction device 601 may employ two or microphones in which the phases and amplitudes of the signals from the microphones are manipulated to provide a beam shape directed towards the patient's good ear. It should be noted that the beam shape 601 is a simplified beam shape illustrated to show that bone conduction device 601 may use two or more microphones configured as a directional microphone configured with a beam shape (also sometimes referred to as a directivity) directed towards the patient's good ear. Two or more microphones operating in tandem are also sometimes referred to as a microphone array.

Or, in a third example, bone conduction device 401 may assume that all sounds received by the microphone of the bone conduction device 401 originated on the opposite side of the patient's head and thus have been attenuated by the head shadow effect. Using such an assumption, the bone conduction device 401 may estimate the sound at the patient's good ear by applying a gain curve that is the inverse of the head shadow effect to sounds arriving at the bone conduction device 401.

In a second example, bone conduction device 401 may compensate for the head shadow effect by employing two or more microphones configured as a directional microphone with a beam shape directed towards the patient's good ear. FIG. 6 illustrates an exemplary beam shape 602 that a bone conduction device 401 may use to receive sounds originating on the opposite side of the patient's head, in accordance with an embodiment. Bone conduction device 401 may use various techniques for employing a directional microphone with a beam shape directed towards the patient's good or functional ear. For example, bone conduction device 401 may employ two or microphones in which the phases and amplitudes of the signals from the microphones are manipulated to provide a beam shape directed towards the patient's good ear. It should be noted that the beam shape 602 is a simplified beam shape illustrated to show that bone conduction device 401 may use two or more microphones configured as a directional microphone configured with a beam shape (also sometimes referred to as a directivity) directed towards the patient's good ear. Two or more microphones operating in tandem are also sometimes referred to as a microphone array.

Figure 7:
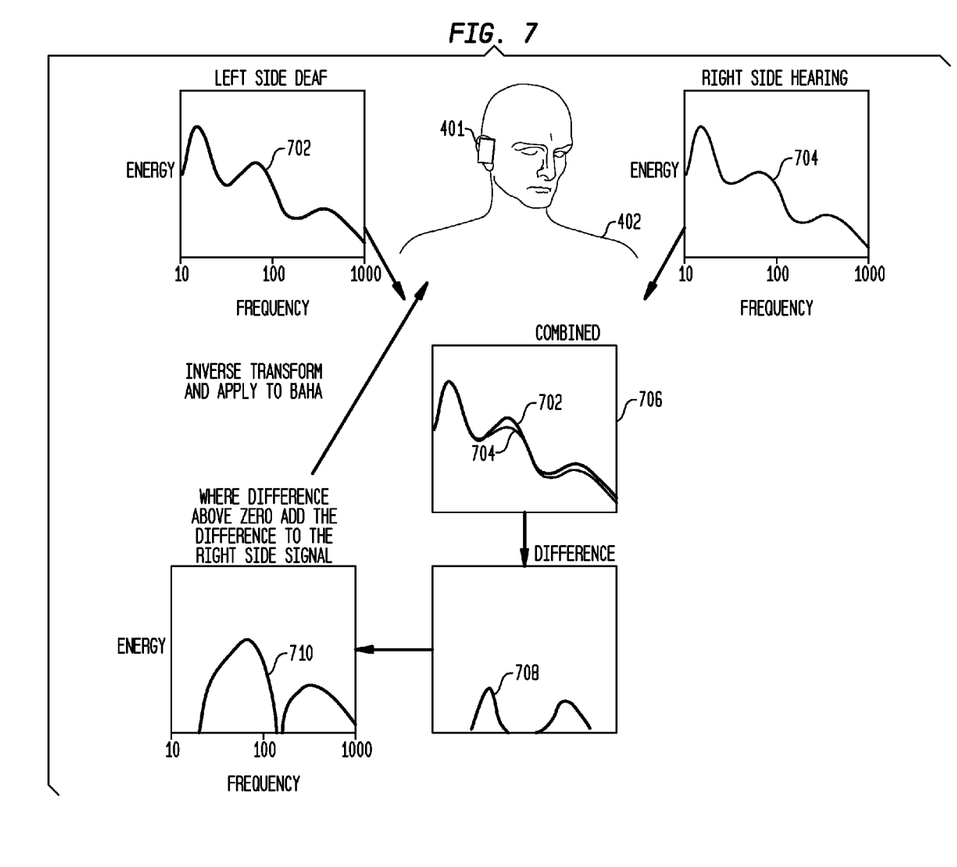
FIG. 7 illustrates an exemplary scheme that a bone conduction device may use to compensate for masking in determining the stimulation to be applied by the bone conduction device, in accordance with an embodiment.

FIG. 7 also illustrates a curve 704 for an exemplary sound signal that may be received by a patient's good ear. This curve 704 similarly varies in intensity by frequency. Further, this curve may be determined by the bone conduction device 401 using the techniques discussed above, such as, using a microphone positioned at the patient's good ear, a directional microphone (e.g., two or more microphones with a beam shape directed towards the patient's good ear), or estimating the signal using the assumption that the sound originated on the side of the patient's good ear.

Box 706 illustrates both curve 702 and 704 overlaid with one another to more readily show the differences between the two sounds. Curve 708 illustrates the difference between the two sounds represented by curves 702 and 704. In this example, there are two frequency regions in which the sound from the patient's deaf side is greater than the sound from the patient's good side. A first region begins at approximately 50 Hz, has a peak at approximately 100 Hz and falls back to 0 at about 150 Hz. The second region begins at approximately 250 Hz, has a peak at about 500 Hz, and falls back to 0 at about 750 Hz.

Using this calculated difference, bone conduction device 401 may filter and apply gain to the sound represented by curve 702 such that the bone conduction device 401 will apply stimulation so that the difference is heard by the good ear. In an embodiment, the gain applied by the bone conduction device 401 to the difference between the two sounds may be to compensate for the head shadow effect. For example, bone conduction device 401 may apply a constant gain to the difference 708, or, for example, a gain in accordance with gain curves 502 or 504 discussed above with reference to FIG. 5. Curve 710 illustrates a curve 710 representative of the stimulation that bone conduction device 401 may apply so that the difference is heard at the good ear.

In a further embodiment, a bone conduction device 401 may use a psychoacoustic model in determining or estimating whether sounds arriving at the patient's deaf ear (i.e., the patient's ear to which the bone conduction device 401 is attached) would be masked by sounds arriving at the patient's good ear. The term "psychoacoustic model" as used herein refers to a mathematical model of the masking properties of the human auditory system. Exemplary psychoacoustic models include, for example, the MPEG-1 Psychoacoustic Model 1, and the MPEG-2 Psychoacoustic Model 2. A more detailed description of exemplary psychoacoustic models can be found in Bernd Edler, Heiko Purnhagen, and Charalampos Ferekidis, *ASAC—Analysis/Synthesis Audio Codec for Very Low Bit Rates*, 100th AES Convention, Copenhagen (May 1996); and Frank Baumgarte, Charalampos Ferekidis, and Hendrik Fuchs, *A Nonlinear Psychoacoustic Model Applied to the ISO MPEG Layer* 3 *Coder,* 99th AES Convention, New York, October 1995 (hereinafter "the Baumgarte reference"), both of which are hereby incorporated by reference herein.

Figure 8:
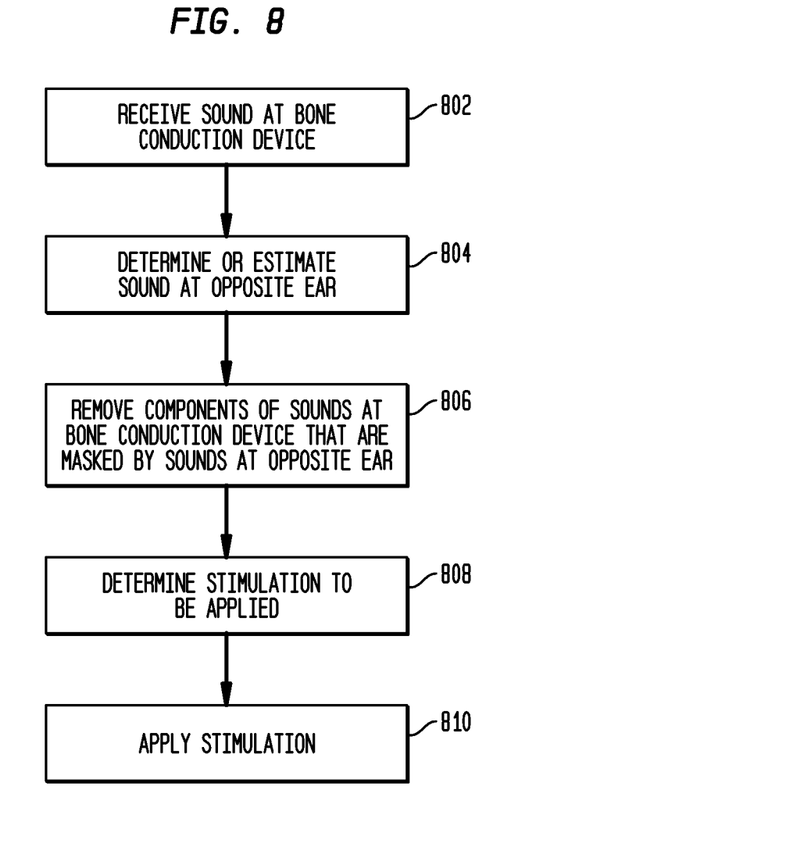
FIG. 8 provides an exemplary flow chart of a method that a bone conduction device may use in determining stimulation to be applied.

FIG. 8 provides an exemplary flow chart of a method that a bone conduction device may use in determining stimulation to be applied. At block 802, bone conduction device 401 receives a sound that may, for example, be described by curve 702 of FIG. 7.

At block 804, bone conduction device 401 determines the sound at the patient's functional ear. Bone conduction device 401 may, for example, execute block 804 contemporaneously with block 802.

Bone conduction device 401 may use various techniques for determining or estimating the sound at the patient's functional ear. In a first example, patient 402 may have a microphone located at the patient's good ear that is capable of receiving sound arriving at the patient's good ear and transferring this information to the bone conduction device 401 via a wired or wireless connection such as discussed above.

Or, for example, bone conduction device may comprise two or more microphones configured as a directional microphone with a beam shape (also referred to as a directivity or sensitivity) directed towards the good ear. In such an example, the estimate of the sound arriving at the functional ear may be obtained by the bone conduction device 601 using the plurality of microphones and then manipulating the phase and/or amplitude of the received signals to determine the sound arriving at the good ear. Further, in such a system, the sound arriving at the deaf ear may be obtained by the bone conduction device 601 using the output from one of the microphones, or by manipulating the phases and amplitudes of the signals from the microphones in a different manner such as, for example, to form an omni-directional beam shape, a beam shape directed in the opposite direction of the functional ear, a beam shape directed towards the front of the patient, or, in some other manner. These two different signals (i.e., the signal for the sound at the good ear and the signal for the sound at the bad ear may be obtained using the same microphones and splitting the signals from the microphones along two different paths (e.g., one path for the functional ear and one for the deaf ear).

In another example, the sound arriving a the good ear may be determined by the bone conduction device 401 using a single microphone and assuming that sound received at the deaf ear originated on the side of the patient's good ear. The bone conduction device 401 may then apply a gain function to the sound received at the deaf ear to provide an estimate of the sound arriving at the good ear. This gain function may be based on the head shadow effect for the patient, and may be for example, a gain curve such as curve 502 of FIG. 5.

Because, the assumption that all sound originates on the side of the patient's good ear is often false or only partially correct, in an embodiment, the bone conduction device 401 may comprise a user interface that permits the patient 402 to adjust the gain function applied for estimating the sound arriving at the good ear. This user interface may, for example, comprise a dial that the patient may adjust in one direction to increase the gain (e.g., raise curve 502) or rotate in the opposite direction to decrease the gain (e.g., drop curve 502).

Or, for example, bone conduction device 401 may include a more complex user interface that permits the patient to adjust the gain in a more complicated manners, such as increasing or decreasing the gain by different amounts for different frequencies or frequency bands. Thus, using the user interface, the patient 402 may be able to adjust the gain themselves to help compensate for situations where the assumption that all sound originate on the side of the patient's good ear is incorrect.

After determining the sound arriving at the good ear and the sound arriving at the deaf ear, at block 806, bone conduction device 401 may remove components of the sound arriving at the bone conduction device that would be masked by sounds arriving at the good ear. As noted above, bone conduction device 401 may use a psychoacoustic model in determining how the sounds arriving at the good ear will mask the sounds received at the deaf ear.

In a further embodiment, bone conduction device 401 may analyze the frequency spectrum of the determined sound for the good ear and locate the peaks of the frequency spectrum. For example, referring to curve 704 of FIG. 7, curve 704 includes three peaks, a first peak is located at approximately 50 Hz, a second peak is located at approximately 100 Hz, and a third peak is located at approximately 750 Hz. Bone conduction device 401 may then use a psychoacoustic model to determine the masking curves for each of the located peaks. This masking curve may, for example, depend on the frequency and amplitude of the peak. Bone conduction device 401 may then apply these masking curves to the sound arriving at the bone conduction device 401 to determine the sounds for which to apply stimulation.

After determining the sound arriving at the bone conduction device 401 that will not be masked, bone conduction device 401 may then determine the stimulation to be applied so that the patient will perceive the unmasked sounds at block 808. Bone conduction device 401 may use techniques such as discussed above with reference to FIGS. 1-3 in determining the stimulation signals for directing the transducer of the bone conduction device 401 to apply stimulation so that the patient will perceive the unmasked sounds. Then, at block 810, bone conduction device 401 applies the stimulation in accordance with the determined stimulation signal.

All documents, patents, journal articles and other materials cited in the present application are hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for operating a bone conduction device fitted to a deaf ear of a patient having a second functional ear comprising:

receiving a sound at the deaf ear, wherein the sound has a plurality of frequency components;

generating an estimate of sound received at a second ear of the patient;

determining, based on the estimate, whether the sound received at the second ear would mask one or more of the frequency components of the sound received at the deaf ear; and determining a set of bone conduction stimulation signals based only on frequency components of the sound received at the deaf ear that would not be masked by the sound received at the second ear.

2. The method of claim 1 wherein determining a set of bone conduction stimulation signals further comprises:

applying a gain to the determined stimulation signals.

3. The method of claim 2, wherein the applied gain varies based on frequency; and wherein applying the gain comprises:

applying a higher amount of gain to one or more higher frequency components than a lower amount of gain applied to one or more lower frequency components.

4. The method of claim 3, wherein the applied gain is determined based on a head shadow effect.

5. The method of claim 1, wherein generating an estimate of sound received at the second ear of the patient comprises:

receiving, with a microphone positioned at the second ear, the sound arriving at the second ear.

6. The method of claim 1, wherein generating an estimate of sound received at the second ear of the patient comprises:

receiving sound using two or more microphones configured to provide a beam shape directed towards the second ear.

7. The method of claim 1, wherein generating an estimate of sound received at the second ear of the patient comprises:

receiving a sound at one or more microphones;

applying a gain to the sound received at the one or more microphones, wherein the applied gain compensates, at least in part, for a head shadow effect.

8. A bone conduction device configured to be fitted to a deaf ear of a patient having a second functional ear comprising:

a sound input device configured to receive, at the deaf ear, a sound having a plurality of frequency components;

an electronics module configured to generate an estimate of sound received at a second ear of the patient, and configured to determine, based on the estimate, whether the sound received at the second ear would mask one or more of the frequency components of the sound received at the first ear, and configured to determine a set of bone conduction stimulation signals based only on one or more frequency components of the sound received at the deaf ear that would not be masked by the sound received at the second ear.

9. The bone conduction device of claim 8, wherein the electronics module is further configured to apply a gain to the determined set of stimulation signals.

10. The bone conduction device of claim 9, wherein the electronics module is configured to apply a gain that varies based on frequency such that the electronics module is configured to apply a higher amount of gain to one or more higher frequency components than a lower amount of gain that the electronics module is configured to apply to one or more lower frequency components.

11. The bone conduction device of claim 10, wherein the gain is based on a head shadow effect.

12. The bone conduction device of claim 8, wherein the bone conduction device comprises a second microphone positioned at the second ear of the patient, and wherein the electronics module is configured to generate an estimate of sound received at a second ear of the patient based on sound received at the second microphone.

13. The bone conduction device of claim 8, wherein the sound input device comprises two or more microphones configured to provide a beam shape directed towards the second ear; and wherein the electronics module is configured to generate an estimate of sound received at a second ear of the patient based on sound received by the two or more microphones.

14. The bone conduction device of claim 8, wherein the electronics module is configured to generate an estimate of sound received at a second ear of the patient based on sound received from the sound input device, and configured to apply a gain to the sound, wherein the applied gain compensates, at least in part, for a head shadow effect.

15. A bone conduction device configured to be fitted to a deaf ear of a patient having a second functional ear, comprising:

means for receiving a sound having a plurality of frequency components;

means for generating an estimate of sound received at a second ear of the patient;

means for determining, based on the estimate, whether the sound received at the second ear would mask one or more of the frequency components of the sound received at the deaf ear; and means for determining a set of bone conduction stimulation signals based only on frequency components of the sound received at the deaf ear that would not be masked by the sound received at the second ear.

16. The bone conduction device of claim 15, wherein the means for determining a set of bone conduction stimulation signals further comprises:

means for applying a gain to the determined stimulation signals.

17. The bone conduction device of claim 16, wherein the applied gain varies based on frequency; and wherein the means for applying the gain comprises:

means for applying a higher amount of gain to one or more higher frequency components than a lower amount of gain applied to one or more lower frequency components.

18. The bone conduction device of claim 17, wherein the applied gain is determined based on a head shadow effect.

19. The bone conduction device of claim 15, wherein the means for generating an estimate of sound received at the second ear of the patient comprises:

a microphone positioned to receive sound arriving at the second ear.

20. The bone conduction device of claim 15, wherein the means for generating an estimate of sound received at the a second ear of the patient comprises:

two or more microphones configured to provide a beam shape directed towards the second ear.

* * * * *